(12) United States Patent
Bange et al.

(10) Patent No.: US 8,379,539 B2
(45) Date of Patent: Feb. 19, 2013

(54) METHODS AND SYSTEMS FOR PROVIDING MULTIPLE ACCESS WITHIN A NETWORK

(75) Inventors: Joseph E. Bange, Eagan, MN (US); Allan T. Koshiol, Lino Lakes, MN (US); Paul Holmquist, Andover, MN (US); Karen M. Kramer, Marine on Saint Croix, MN (US); Thomas J. Harris, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 912 days.

(21) Appl. No.: 12/477,754

(22) Filed: Jun. 3, 2009

(65) Prior Publication Data

US 2009/0296602 A1 Dec. 3, 2009

Related U.S. Application Data

(60) Provisional application No. 61/058,499, filed on Jun. 3, 2008.

(51) Int. Cl.
*H04L 12/28* (2006.01)
*H04L 12/413* (2006.01)
*H04W 4/00* (2009.01)

(52) U.S. Cl. .......................... 370/254; 370/338; 370/445

(58) Field of Classification Search ........................ None
See application file for complete search history.

(56) References Cited

U.S. PATENT DOCUMENTS

| | | | |
|---|---|---|---|
| 6,650,944 B2 | 11/2003 | Goedeke et al. | |
| 6,804,558 B2 | 10/2004 | Haller et al. | |
| 2002/0044549 A1* | 4/2002 | Johansson et al. | 370/386 |
| 2002/0176445 A1* | 11/2002 | Melpignano | 370/480 |
| 2003/0036350 A1* | 2/2003 | Jonsson et al. | 455/41 |
| 2007/0260293 A1 | 11/2007 | Carpenter et al. | |
| 2008/0109051 A1 | 5/2008 | Splinter et al. | |
| 2009/0058635 A1 | 3/2009 | LaLonde et al. | |
| 2009/0063187 A1 | 3/2009 | Johnson et al. | |
| 2011/0313491 A1* | 12/2011 | Bange et al. | 607/59 |

OTHER PUBLICATIONS

"Serial Infrared Link Access Protocol (IrLAP)", (Version 1.1), Infrared Data Associationsm, (Jun. 16, 1996), 116 pgs.
Bharghavan, V., et al., "MACAW: A Media Access Protocol for Wireless LAN's", *Proceedings of the Conference on Communications Architectures, and Protocals and Applications (SIGCOMM '94)*, (1994), 212-225.

\* cited by examiner

*Primary Examiner* — Steven H Nguyen
(74) *Attorney, Agent, or Firm* — Schwegman Lundberg & Woessner, P.A.

(57) ABSTRACT

Methods and systems for media access control allow master and slave nodes of a network to communicate using the same carrier while avoiding collisions of transmissions. At least one slave node is an implantable device. Master nodes initiate all data exchange sequences, and slave nodes are responsive to the data exchange sequences. The exchange sequences begin by master nodes contending for use of the carrier through a countdown procedure. A set order of communications occurs between a master node who won the contention and a slave node being communicated with by the master node to transfer a data frame. Contention is then repeated to determine the next master node that is allowed to transfer a data frame. New master nodes entering the network employ a discovery process to poll for existing devices in the network.

20 Claims, 10 Drawing Sheets

METHODS AND SYSTEMS FOR PROVIDING MULTIPLE ACCESS WITHIN A NETWORK

RELATED APPLICATIONS

This application claims the benefit under 35 U.S.C. 119(e) of U.S. Provisional Patent Application Ser. No. 61/058,499, filed on Jun. 3, 2008, which is incorporated herein by reference in it entirety.

TECHNICAL FIELD

The present invention is related to communicating between two nodes of a network using a carrier wave. More particularly, the present invention is related to communicating in a network of medical devices between a master node and a slave node where contention for the carrier of the network occurs between multiple master nodes.

BACKGROUND

Radio Frequency (RF) communications between nodes of a network typically require a carrier wave to be used to transport data signals from one node to the next. However, nodes of a network may not be frequency agile so that multiple nodes must communicate using the same carrier frequency. This may be especially true for wireless networks of medical devices where the availability of radio frequency spectrum is limited due to technological and regulatory reasons. The lack of frequency agility may be necessary to maintain communications within an allotted spectrum and/or to reduce the complexity and cost of the transceivers of the network nodes.

For communications between many nodes to occur through using the same carrier, collisions of the communications must be avoided. Collisions occur where two or more nodes attempt to transmit at the same time on the same carrier so that a receiving node is exposed to multiple transmissions simultaneously. The multiple transmissions cannot be individually decoded at the receiving node because they interfere with one another. Thus, to prevent collisions, the multiple nodes within range of one another who utilize the same carrier must operate so that only a single node transmits on the carrier at a given time.

To synchronize transmissions, nodes must not simply transmit at any time when a transmission may be desired. The nodes must have some ability to determine when another node is about to transmit on the carrier to avoid transmitting at the same time. This synchronization of transmissions is further complicated when nodes come and go within a network, which is typical within a wireless network, and when transmissions between nodes have varying degrees of urgency.

Overview

Embodiments of the present invention address these and other problems of a network where multiple nodes utilize the same carrier. Embodiments provide methods and systems where nodes of the network are either master nodes or slave nodes. Master nodes are those who initiate the exchange sequences with a slave node. A slave node is responsive to an initiation of an exchange sequence by a master node. A set order of communications occurs between a master node and a slave node in an exchange sequence to allow the data to be exchanged and to avoid other master and slave nodes within range from transmitting at the same time as the exchange sequence.

One embodiment of the present invention is a method of discovering nodes to establish communication between a first master node and one or more nodes in a network medium used by a plurality of master nodes and slave nodes where contention for a carrier of the network medium occurs between the plurality of master nodes. The method involves at a first master node, contending for the carrier until winning. After winning at the first master node, the first master node sends out a plurality of discovery access codes. The first master node sends out a request for request to send message containing a first discovery access code of the plurality and listens for a request to send message containing the first discovery access code. The first master node sends out a clear to send message upon receiving the request to send message. Upon receiving a data send message in response to the clear to send message at the first master node, when the data send message is from a second master node and includes a list of session access codes in use by the second master node, the first master node excludes the list of session access codes in use by the second master node from a list of potential session access codes. Upon receiving the data send message in response to the clear to send message at the first master node, when the data send message is from a first slave node that includes identification information for the first slave node, the first master node stores the first slave node identification information in preparation for associating with a session access code that is not excluded from the list of potential session access codes.

Another embodiment is a method of discovering nodes to establish communication between a first master node and one or more nodes in a network medium used by a plurality of master nodes and slave nodes where contention for a carrier of the network medium occurs between the plurality of master nodes. At a second master node of the plurality, a transmission of a set of discovery access codes is received. The second master node randomly chooses one of the discovery access codes from the set. Upon receiving a request for request to send message at the second master node that contains the randomly chosen discovery access code, the second master node sends a request to send message that contains the randomly chosen discovery access code. Upon receiving a clear to send message at the second master node, the second master node sends a data send message containing a list of session access codes currently in use by the second master node.

Another embodiment is a method of discovering nodes to establish communication between a first master node and one or more nodes in a network medium used by a plurality of master nodes and slave nodes where contention for a carrier of the network medium occurs between the plurality of master nodes. The method involves receiving, at a first slave node of the plurality, a transmission of a set of discovery access codes. The first slave node determines whether the first slave node is already in a session. When the first slave node detects that it is not already in a session, then the first slave node randomly chooses one of the discovery access codes from the set. Upon receiving a request for request to send message at the first slave node that contains the randomly chosen discovery access code, the first slave node sends a request to send message that contains the randomly chosen discovery access code. Upon receiving a clear to send message at the first slave node, the first slave node sends a data send message containing a node identifier.

Another embodiment is a system for discovering nodes to establish communication between a first master node and one or more nodes in a network medium used by a plurality of master nodes and slave nodes where contention for a carrier of the network medium occurs between the plurality of master nodes. The system includes first means at the first master node for providing discovery access codes to the plurality of master and slave nodes and for polling the master and slave nodes using the discovery access codes to obtain the node identifier of slave nodes not in a session and to obtain the session access codes in use by the master nodes. The system includes a second means at the master nodes for responding to the first master node when the discovery access code of each master node is polled by the first means, wherein the response from the second means provides the session access codes in use by the master nodes. The system also includes a third means at the slave nodes for responding to the first master node when the discovery access code of each slave node is polled by the first means, wherein the response from the third means provides a node identifier of each slave node to be associated by the first means with a session access code that has not been excluded.

Another embodiment is a method of establishing communication between a first master node and one or more nodes in a network medium used by a plurality of master nodes and slave nodes where contention for a carrier of the network medium occurs between the plurality of master nodes. The method involves at the first master node, contending for the carrier until winning. After winning, the first master node sends a request to send message with a universal access code. The request to send with the universal access code is received at the plurality of master and slave nodes. After sending the request to send message, the first master node sends a clear to send message. The clear to send message with the universal access code is received at the plurality of master and slave nodes. After sending the request to send message, the first master node sends a data send message, wherein data of the data send message specifies a node identifier corresponding to a node and specifies an access code. The data send message is received at the plurality of master and slave nodes. It is detected at the plurality of master and slave nodes whether the node identifier is a match. For the node that detects that the node identifier is a match, the access code is utilized to identify communication from the first master node that also contains the access code.

Another embodiment is a method of communicating between a first master node and a first slave node where contention for a carrier of a network medium occurs between a plurality of master nodes. The method involves at the first master node, contending for use of the carrier. Upon winning contention of the carrier, the first master node sends a request to send message with a session access code corresponding to the first slave node. The first master node receives a clear to send message after sending the request to send message. Upon receiving the clear to send message at the first master node, the first master node sends a data send message, wherein the data send message contains data for use by the first slave node. The first master node receives an acknowledgement message after sending the data send message.

Another embodiment is a method of communicating between a first master node and a first slave node where contention for a carrier of a network medium occurs between a plurality of master nodes. The method involves at the first slave node, receiving a request to send message having an access code. The first slave node determines whether the access code of the request to send message corresponds to the first slave node. After determining that the access code of the request to send message does correspond to the first slave node, the first slave node sends a clear to send message. After sending the clear to send message, the first slave node receives a data send message containing data to be utilized by the first slave node. After receiving the data send message, the first slave node sends an acknowledge message.

Another embodiment is a system for communicating between a first master node and a first slave node where contention for a carrier of a network medium occurs between a plurality of master nodes. The system includes a first means at the first master node for sending a request to send message with an access code of the first slave node when data is to be sent to the first slave node and a request for request to send message with the access code when data is to be sent from the first slave node. The first means is also for sending a data send message after receiving a clear to send message and for sending an acknowledge message after receiving a data send message. The system also includes a second means at the first slave node for receiving the request to send message and the request for request to send message, detect that the access code corresponds to the first slave node, send a clear to send message after receiving a request to send message, send a request to send message after receiving a request for request to send message, send an acknowledge message after receiving a data send message, and send a data send message after receiving a clear to send message.

Another embodiment is a method of contending for use of a carrier of a network medium where contention for the carrier occurs between a plurality of master nodes. The method involves at a first master node, randomly choosing a value between a minimum and a maximum. The first master node detects whether the carrier begins or continues to be in use. The first master node begins a countdown from the randomly chosen value when the first master node detects that the carrier is not in use. While counting down from the randomly chosen value at the first master node, the first master node detects whether the carrier begins to be in use. When use of the carrier is detected at the first master node, the first master node pauses counting down while it is determined that the carrier continues to be in use. When the countdown at the first master node reaches a win value, the first master node transmits a message using the carrier.

Another embodiment is a method of synchronizing contention for use of a carrier of a network medium where contention for the carrier occurs between a plurality of master nodes. The method involves at a first master node, contending for the carrier until winning. Upon winning, the first master node sends a first message. The first master node starts a timeout timer and a first contention timer upon sending the first message. If a second message is not received at the first master node before the timeout timer expires, then the first master node begins contending for the carrier again upon the expiration of the first contention timer. If the second message is received at the first master node before the timeout timer expires, then the first master node sends a third message and sets a second contention timer. The first master node begins contending for the carrier again upon the expiration of the second contention timer.

Another embodiment is a system for contending for use of a carrier of a network medium where contention for the carrier occurs between a plurality of master nodes. The system includes a first means at a first master node for randomly choosing a first value, counting down from the first value when the carrier is not in use within the network medium, pausing the countdown when the carrier is in use, and transmitting a first message when the countdown reaches a win value. The system also includes a second means at a first slave node for receiving the first message and sending a second message on the carrier upon receiving the first message.

Another embodiment is a method of terminating communication between a first master node and a first slave node in a network medium in use by a plurality of master and slave nodes where contention for a carrier of a network medium occurs between a plurality of master nodes. The method involves at the first master node, contending for the carrier until winning. After winning, the first master node sends a request to send message with an access code identifying the first slave node. The request to send message with the access code is received at the plurality of master and slave nodes. The first slave node detects that the request to send message contains the access code of the first slave node. In response to detecting the access code at the first slave node, the first slave node sends a clear to send message. The first master node receives the clear to send message. In response to receiving the clear to send message, the first master node sends a data send message, wherein the data send message specifies a disconnect command. The first slave node receives the data send message. In response to receiving the data send message, the first slave node sends an acknowledge message and discards the access code. The first master node receives the acknowledge message and in response to receiving the acknowledge message, identifies the access code as no longer being in use.

DETAILED DESCRIPTION

Figure 1:
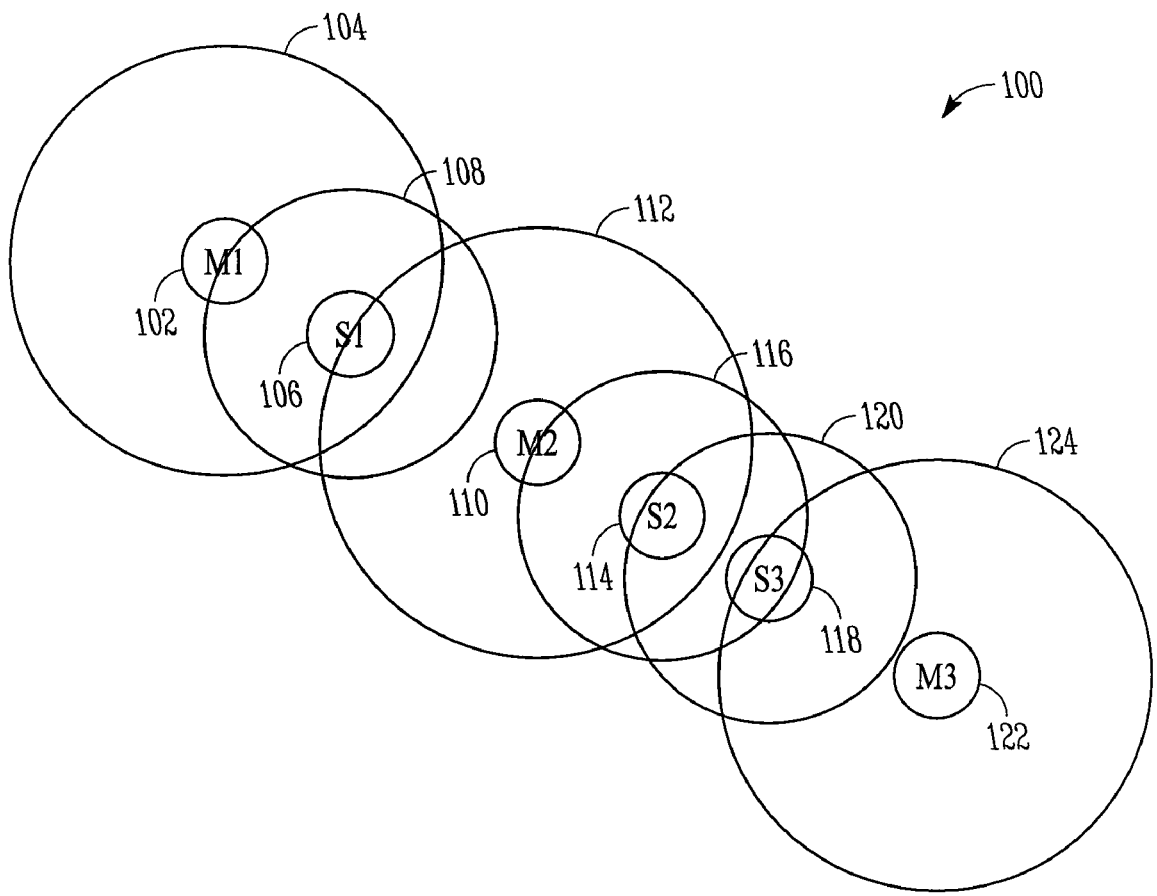
FIG. 1 illustrates a typical network operating environment including master and slave nodes according to the present invention.

Embodiments of the present invention provide access to a carrier of a network medium for multiple nodes while avoiding collisions of transmissions from the nodes and while providing reattempts when collisions do occur. The nodes of the network include master nodes and slave nodes.

The slave nodes include implantable medical devices designed to be implanted into a patient. Some examples of these devices include cardiac function management (CFM) devices such as implantable pacemakers, implantable cardioverter defibrillators (ICDs), cardiac resynchronization therapy devices (CRTs), and devices that include a combination of such capabilities. The devices can be used to treat patients using electrical or other therapy or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. Other examples of implantable devices include implantable diagnostic devices, implantable drug delivery systems, or implantable devices with neural stimulation capability.

The master nodes include external devices to communicate with slave nodes and other master nodes using far-field RF telemetry. Some examples of these devices include an implantable device programmer, a repeater, or a network device to provide advanced patient care management (e.g., a server). The master nodes initiate the communications sequences to exchange information with slave nodes. The slave nodes only communicate with master nodes. The slave nodes are unable to initiate communications sequences, but respond to the initiation of the communications sequences of a master node accordingly.

The network may be a wireless network where wireless RF electromagnetic carriers are used to transport data signals. The network may also be a wired network where RF electrical carriers are used to transport the data signals. The devices that are encompassed within the network from the perspective of a master node are the devices that the operation of the master node must consider when attempting to transmit and receive to avoid collisions. Because the master node can cause a second node to transmit, the operation of the master node must account for the nodes within communication range of the second node and outside the range of the master node (i.e., hidden nodes) when determining how to complete exchange sequences.

Various communication states may be used in one or more embodiments to facilitate the communication between the master and slave nodes to avoid collisions and reattempt exchanges when collisions occur. A discovering state for a master node allows the master node to determine which slave node to communicate with and the available session access codes to be used to communicate with one or more slave nodes. The discovering state allows a new master node to enter a network or a master node in the network to detect a new slave node within the network. A discovered state for a master node allows the master node to inform a discovering master node about which session access codes are reserved or in use by the discovered master node. A discovered state for a slave node allows the slave node to ignore the discovering master node if the slave node is already in a session with another master node or to provide node identification to the discovering master node if the slave is available for a communication session.

A connection state for a master and slave node allows the master node to assign a session access code to a slave node that will allow the master node to exchange data with the slave node rather than other nodes of the network. The session access code should have been determined to be available to uniquely identify communications between the master and slave node through the master node entering the discovery state to determine the slave node is available for a session and to determine the session access codes that are not reserved by other master nodes in the network.

A session state for a master node allows the master node to initiate exchanges for a session with a slave node. The master node initiates an exchange when the master node has data to send to the slave node, when the master node is aware that the slave node has data to send to the master node, and when the master node reaches a time to poll the slave node for data. The session state for a slave node allows the slave node to receive data sent by the master node, send data to the master node when data is requested, inform the master node when more data is available for sending to the master node, and inform the master node when the slave has no data to send.

A disconnect state for a master and slave node allows the master node to inform the slave node that the communication session is to be terminated so that no attempts at any additional communication exchanges will be attempted. This allows the session access code in use between the master and slave node to be made available for use in the network between the master node and another slave node and allows the slave node to identify itself to other master nodes as being available for a communication session.

During these states, the master node attempts contention for the carrier so that many nodes of the network are not transmitting on the carrier at the same time. To do so, the master nodes employ contention rules to contend for the carrier before transmitting until a master node wins and then to determine when the next period to contend begins. In doing so, the master nodes each get a turn to complete an exchange with a slave node without other master nodes attempting to transmit on the carrier at the same time. These contention rules may provide for priority so that a master having data of a highest priority to send or to receive can have a higher probability of winning the contention for the carrier. Furthermore, these contention rules may provide for determining that the time for all of the master nodes to again begin contending for the carrier should occur at the anticipated end of an ongoing exchange between a master and slave node or earlier in situations where the exchange has been attempted but failed before completion.

During exchanges within these communication states, the master and slave nodes employ communication rules that expect communications to be received in a particular order in relation to specific types of communications messages that the master and slave nodes send. Upon the master node not receiving an expected message from the slave node, the operation of the master node recognizes that the exchange failed and reattempts the exchange after again contending for the carrier.

These various communications states, contention rules, and communication rules and the associated network, master nodes, and slave nodes are discussed in greater detail below with references to FIGS. 1-11. The discussion below provides an example of a network system including a plurality of master and slave nodes that perform various logical operations to bring about the various communication states and employ the contention rules and communication rules. Although the discussion below provides an example of the integration of each of the various states and rules into a network system, the discussion and example of this integration of states and rules is intended to be illustrative and is not to be taken in a limiting sense.

FIG. 1 shows a network 100 of master and slave nodes using the same carrier frequency for transmitting signals. The master and slave nodes of the network 100 as shown communicate wirelessly such that the nodes shown are not able to receive transmissions from all nodes present. As shown for this example, the master and slave nodes have transmission ranges, and the master nodes have a greater transmission range than the slave nodes.

A typical example of this is where the slave node is an implantable device (e.g., a cardiac function management device such as a pacemaker or implantable cardioverter defibrillator) and a master node is an external device programmer or repeater. Frequencies used in communications between such devices may be limited, such as to the industrial, scientific, and medical (ISM) band for example. An approach to communicating with an implantable medical device using an external device is found in Carpenter et al., U.S. Patent Pub. No. 2007/0260293, "Configurable Medical Telemetry Radio System," filed May 3, 2006, which is incorporated herein in its entirety.

An implantable device is typically battery powered and is designed to use as little power as possible during operation. Also, transmissions from an implantable device may be attenuated by the housing of the device and by body tissue. For these reasons, the range of transmission of a slave node in this example is much lower than the range of a master node. It will be appreciated that master and slave nodes may have equal transmission ranges in other examples. It will also be appreciated that the implantable medical devices are mobile with the patient. This means that slave nodes may be added and subtracted from a given network at a frequent rate.

There may be different levels of priority for the data to be communicated between a master node and a slave node. In the example where the master node is a programmer or repeater and the slave node is an implantable medical device, several priority levels may be according to varying levels of urgency of the data. The highest priority of data may be urgent data, such as a command to provide a stat pace or a stat shock to the patient for example. The next highest level of priority may include data to be transmitted in real time, such as internal electrogram (egram) data or event markers for example. The next level of priority includes device user initiated transfers, such as programming and interrogation data for example. The lowest level of priority may include background data, such as non-user initiated data transfers used to collect data when the carrier or the network medium is otherwise idle.

In the example shown in FIG. 1, a master node 102 has a transmission range 104. A slave node 106 intended for communication with the master node 102 and falling within the transmission range 104 has a transmission range of 108, which also reaches the master node 102. Thus, bi-directional communication can be established between the master node 102 and slave node 106 as they are currently positioned.

Master node 110 is present and has a transmission range 112. Slave node 114 is intended for communication with the master node 110 and falls within the transmission range 112. Slave node 114 has a transmission range of 116, which reaches the master node 110 enabling bi-directional communication. However, the transmission range 112 of the master node 110 also reaches the slave node 106, which is intended to communicate with the master node 102. Thus, slave node 106 is subject to receiving collisions if master node 102 and master node 110 transmit at the same time.

Master node 122 is present and has a transmission range 124. Slave node 118 is intended for communication with the master node 122 and falls within the transmission range 124. However, slave node 118 has a transmission range 120 that does not reach to master node 122. Therefore, slave node 118 can receive transmissions from master node 122 but cannot successfully respond to master node 122. Transmission range 120 of slave node 118 does reach slave node 114, so slave node 114 is subject to receiving collisions if master node 110 and slave node 118 transmit at the same time.

These master and slave nodes employ a media access control subsystem or system to control use of the carrier within a network 100 to avoid collisions. The media access control system is typically implemented within a data link layer of a communication stack that is employed by the master and slave nodes.

Figure 2:
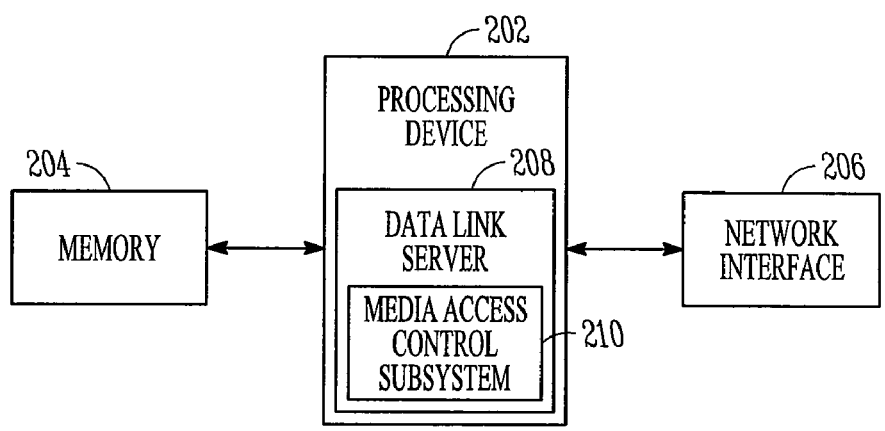
FIG. 2 illustrates the components of embodiments of the master and slave nodes of FIG. 1.

FIG. 2 shows the components for embodiments of master and slave nodes that implement the communication stack including the data link layer providing media access control. The master and slave nodes include at least one processing device 202. The processing device 202 may be a general-purpose programmable processor for implementing code stored in memory 204, may be hard-wired digital logic, or any combination. The processing device 202 performs logical operations to implement the data link layer 208 as well as any other layers of the communication stack that may be present. For example, the processing device 202 may also implement a network layer to provide a network routing such as an Internet Protocol ("IP") address for data packets and may implement a transport layer to provide data packets with transport control such as a Transmission Control Protocol ("TCP") header. Additionally, the processing device 202 may implement application layer programs that produce data to be transmitted to other nodes and that utilizes data that is received from other nodes.

As discussed above, the nodes include memory 204 that is utilized by the processing device 202. The memory 204 contains random access memory, read only memory, or any combination. The memory 204 may be used to store programming for the processing device 202. Furthermore, the memory 204 may be used to store information used by the processing device 202 during execution of the various layers of the communication stack, such as application, transport, network, and data link information.

The processing device 202 sends and receives transmissions through a network interface 206. The network interface 206 includes physical layer components for passing raw bits over the carrier wave in use for the network. The transmitting physical layer may add a preamble to the beginning of a frame such that detection of the preamble at a receiving physical layer of each node in range signifies an incoming frame to each of these. The network interface 206 includes an interface to a medium for transporting the carrier wave. For a wired network, a transceiver is included for sending and receiving electrical signals, whereas for a wireless network, a transceiver is included for sending and receiving electromagnetic signals. The network interface 206 is controlled through operation of the media access control subsystem 210 or system of the data link layer 208 that the processing device 202 is implementing to enable the node to send and receive data and to avoid collisions in the network.

Figure 3:
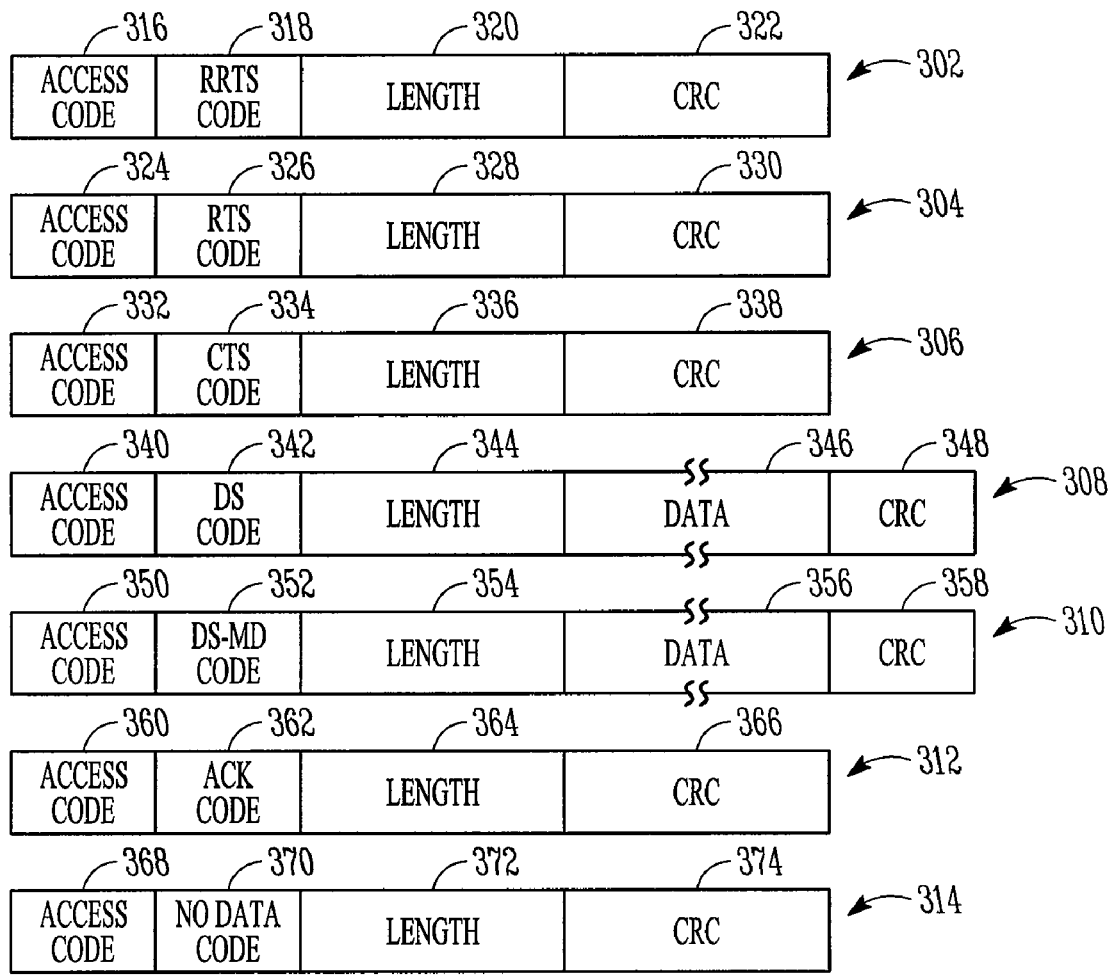
FIG. 3 shows examples of communication frames that are transmitted between master and slave nodes of FIG. 1.

FIG. 3 shows examples of communication frames transmitted and/or received by the data link layer to execute the media access control system. As noted below, some communication frames are transmitted only by master nodes, some frames are transmitted only by slave nodes, and some frames are transmitted by both.

Frame 302 is a request for request to send ("RRTS") message. The RRTS frame 302 is a polling message transmitted only by a master node to signal to a slave node (or another master node during a discovery process) that the master node is requesting the slave node to send any available data. The RRTS also puts other eavesdropping nodes within transmission range on notice of the exchange sequence. The RRTS frame 302 includes an access code portion 316 defined by a set number of bits. The access code is used to identify communications intended for reception by a specific node in the network rather than any node. However, as discussed below, at certain times a universal access code may be used for any or all frames of FIG. 3 when the communication is intended for all nodes within transmission range.

The RRTS frame 302 also includes a frame identifier portion 318 defined by a set number of bits. This portion 318 identifies the frame 302 as the RRTS frame so that the recipient slave node recognizes how to respond to the received frame. A length portion 320 is defined by a set number of bits and specifies the length of data that the master intends the slave to transmit. The length of data being exchanged per exchange sequence may be a dynamic value within the network such that one exchange with a master may have a different length for data than another with the same master and may differ from one master to the next. This length information allows eavesdropping master nodes to be able to compute when an exchange sequence between a master node and slave node will end. The RRTS frame 322 may also include a cyclic redundancy check ("CRC") portion 322 that allows the receiving device to determine that the information in the frame has been properly received.

Frame 304 is a request to send ("RTS") message. The RTS frame 304 is transmitted from a master node to a slave node to inform the slave node that the master is going to send data to the slave node (or send data to a master node during a discovery process). The RTS frame 304 is transmitted from a slave node to a master node in response to receiving an RRTS message if the slave node does have data to send. The RTS frame 304 also puts eavesdropping nodes on notice that the exchange sequence will occur. The RTS frame 304 includes an access code portion like the access code portion 316 of the RRTS frame 302. The RTS frame 304 includes a frame identifier portion 326 that contains a value indicating the frame is an RTS frame. A length portion 328 and CRC portion 330, like length portion 320 and CRC portion 322 of frame 302, are also included in frame 304.

Frame 306 is a clear to send ("CTS") message. The CTS frame 306 is transmitted from a master node to a slave node (or to another master node during a discovery process) in response to receiving an RTS from the slave node or is transmitted from the slave node to the master node in response to receiving an RTS from the master node. The CTS frame 306 also puts eavesdropping nodes on notice that the exchange sequence will occur. The CTS frame 306 includes an access code portion 332 as discussed above. The CTS frame 306 includes a frame identifier portion 334 that provides a value that indicates the frame 306 is a CTS frame. The CTS frame 306 also includes a length portion 336 and CRC portion 338 as discussed above.

Frame 308 is a data send ("DS") message. The DS frame 308 is transmitted from a master node to a slave node (or another master node during a discovery process) in response to receiving a CTS from the slave node to transfer data to the slave node. The DS frame 308 is transmitted from the slave node to the master node in response to receiving a CTS frame from the master node to transfer data to the master node if this is the last data frame the slave has to send. The DS frame 308 also puts other eavesdropping nodes on notice that the exchange sequence is continuing past the RTS-CTS stage. The DS frame 308 includes an access code portion 340 as discussed above. The DS frame 308 includes frame identifier portion 342 that provides a value that indicates the frame 308 is a DS frame. The DS frame 308 also includes a length portion 344 and CRC portion 348. However, the DS frame 308 also includes a data field portion 346 where the data itself for the transmission is included.

Frame 310 is a data send more data ("DS-MD") message. The DS-MD frame 310 is transmitted from the slave node to the master node to transfer data to the master node if the slave node has more data to send. The DS-MD message is the same as the DS message except that the master node is informed that the master needs to send another RRTS at the next opportunity because the slave has more data to send. The DS-MD frame 310 also puts other eavesdropping nodes on notice that the exchange sequence is continuing past the RTS-CTS stage. The DS-MD frame 310 includes an access code portion 350 as discussed above. The DS-MD frame 310 includes a frame identifier portion 352 that provides a value that indicates the frame 310 is a DS-MD frame. The frame identifier portion of the frame may also contain additional control values that are absent or are always zeros for the other frames of FIG. 3. These control values may be set by a slave to indicate the priority of the data that remains to be sent to the master. The DS-MD frame 310 also includes a length portion 354, a data portion 356, and a CRC portion 358 as discussed above.

Frame 312 is an acknowledge ("ACK") message. The ACK frame 312 is transmitted from the master to the slave (or to another master during a discovery process) or from the slave to the master to indicate that a DS message or a DS-MD message has been received. The ACK frame 312 informs the receiving node that the data has been received and can therefore be discarded from the transmission queue. The ACK frame 312 includes an access code portion 360 as discussed above. The ACK frame 312 also includes a frame identifier portion 362 that provides a value that indicates the frame 312 is an ACK frame. The ACK frame 312 also includes a length portion 364 and CRC portion 366 as discussed above.

Frame 314 is a NO DATA message. The NO DATA frame 314 is transmitted from the slave to the master upon the slave receiving an RRTS from the master to inform the master that the slave has no data to send and that the exchange sequence can end without a DS or DS-MD message being exchanged. The NO DATA frame 314 also puts other eavesdropping nodes on notice that the exchange sequence is ending without a DS or DS-MD exchange. The NO DATA frame 314 includes an access code portion 368 as discussed above. The NO DATA frame 314 includes a frame identifier portion 370 that provides a value that indicates that the frame 314 is a NO DATA frame. The NO DATA frame 314 also includes a length portion 372 and CRC portion 374 as discussed above.

Figure 4:
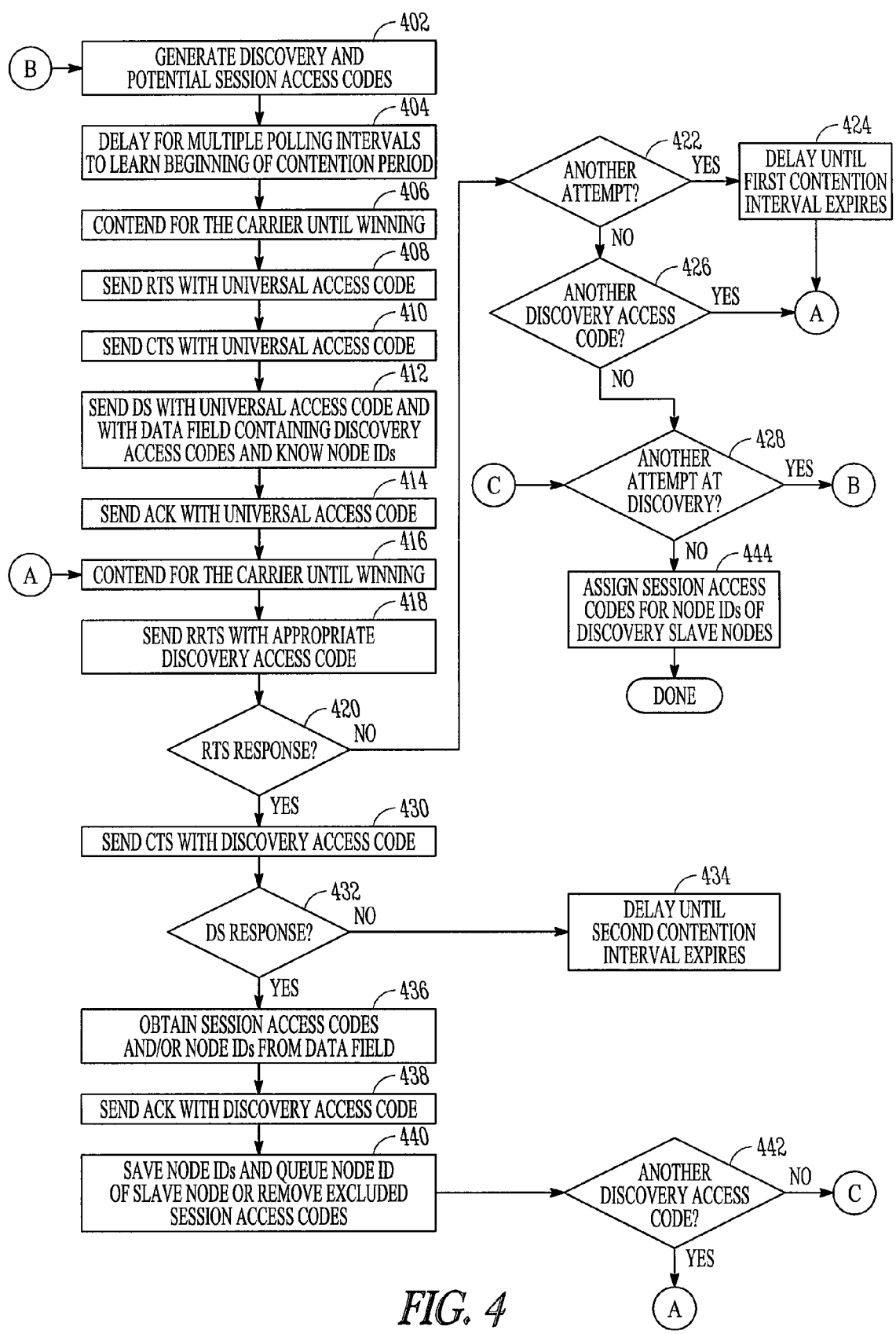
FIG. 4 shows illustrative logical operations performed by a master node attempting to discover other master and slave nodes of the network.

FIG. 4 illustrates an example of the logical operations performed by the processing device of a master node attempting to discover other nodes in the network, such as when the master node is first entering the network or when the master node decides to check for additional nodes that the master may decide to communicate with upon learning which nodes are present.

The logical operations begin at generate operation 402 where the master node generates a set of discovery access codes and potential session access codes. The discovery access codes are access codes that will be used by the master node in the access code portion of transmitted frames to identify existing nodes in the network during the discovery process. Once the master has finished discovering the nodes, the discovery access codes will no longer be used. The potential session access codes are access codes whose availability for use during communication sessions with slave nodes the master will determine during the discovery process.

The number of discovery access codes initially generated is one design choice of many. The more numbers generated initially, the longer the discovery process may take if there are a relatively small number of nodes existing in the network. However, the discovery process may require additional iterations if the initial number of discovery codes are small relative to the number of nodes in the network.

The number of potential session access codes initially generated is also one design choice. However, the number generated is typically more than the number of slave nodes that the master node expects to establish communication sessions with because some of the potential access codes may already be in use in the network and will be excluded from the session access codes that the master can use.

After generating these codes, the master node will then delay for multiple polling intervals to learn the beginning of a contention period at delay operation 404. A polling interval is the time that will pass between a master sending an RRTS and then again sending another RRTS. The master in a network periodically sends an RRTS to the slave node it is in a communication session with because the slave cannot initiate communication with the master but must wait for the master to start the exchange sequence with the RRTS before sending data to the master. Thus, the periodic RRTS allows the master to get any available data from the slave.

The contention period is a period of time when master nodes who wish to start an exchange sequence contend for use of the carrier of the network. This contention is described in more detail with reference to FIGS. 8 and 9. Upon a master node winning contention, the master node transmits the first frame of the exchange sequence, either an RTS or an RRTS. All master nodes start the contention period at the same time, so a new master node entering the network delays for the polling intervals which is long enough to hear at least one frame of the current exchange sequence taking place between a master and slave in the network since at least one RRTS exchange will be attempted. From eavesdropping on the RRTS exchange to learn the length of the DS or DS-MD that will be returned and from learning whether the CTS and/or DS response is sent, the master in the discovery process of FIG. 4 can then determine when the contention period for master nodes starts.

Upon reaching this start of the contention period, the master node in the discovery process of FIG. 4 begins contending for use of the carrier at contend operation 406 until winning. As mentioned, the contention process is discussed in greater detail below with reference to FIGS. 8 and 9. Once contention for the opportunity to transmit on the carrier has been won by the master node, the master node enters a broadcast mode. In broadcast mode the master node sends an RTS message with the universal access code in the access code portion at RTS operation 408. Because all nodes of the network are always eavesdropping, either to determine when to start contention for master nodes or to determine whether to respond if a slave node, the universal access code of the RTS is received by, or broadcast to, all nodes within range. Each node of the network is attentive to the universal access code, and each node then awaits further transmissions by the master node to proceed with the discovery process. The behaviors of the master and slave nodes receiving the RTS with the universal access code are described in more detail with reference to FIGS. 5 and 6.

Upon sending the RTS, the master node of the discovery process of FIG. 4 then continues in broadcast mode by sending a CTS message with the universal access code at CTS operation 410, which indicates to the nodes of the network that a DS message will be sent. Then, the master node sends a DS message with the universal access code at DS operation 412. This DS message has a data field that lists the discovery access codes previously generated by the master node at generate operation 402. For subsequent iterations of the discovery process, this DS message will also contain the node identifier information of previously discovered nodes. However, upon the first iteration for a new master node implementing the discovery process of FIG. 4, no node identifiers will be known so none will be provided in the DS message. A node identifier is a piece of information, such as model and serial number for a device, that uniquely identifies the device among others in the network. However, this model and serial number may not be useful for identifying every frame transmitted to and from a node because this model and serial number may be overly large and therefore create too much overhead for every frame being transmitted. This is useful when implementing a network that includes implantable devices. Reducing the overhead communicated in a message provides a network protocol that allows the devices to communicate using lower power.

Upon sending the DS message, the master node sends an ACK message with the universal access code at ACK operation 414. The broadcast mode exchange sequence is complete so the master node as well as all other master nodes in the network who wish to start an exchange sequence begin contending for use of the carrier at contend operation 416.

Upon the master node winning contention for the carrier, the master node sends an RRTS with one of the discovery access codes included in the access code portion at RRTS operation 418. The master node then determines whether an RTS response has been received prior to a timeout expiring at query operation 420. The timeout is a standard time to wait for a message to be received upon sending another message that requires a response. If the timeout expires, then it may mean that the message that was sent was not received (collided, recipient out of range, or for discovery no node has the discovery access code) or it may mean that a return message was not received (collided or recipient out of range).

If the RTS response was not received before the timeout, then the master determines whether another attempt for the same discovery access code should be attempted at query operation 422. The number of retries for a discovery access code is another design choice. If no node to be discovered has the discovery access code, then more retries wastes more time. If a node to be discovered does have the discovery access code but its response collided, then fewer retries may result in the node not ever being heard during this iteration and discovery of this node must be reattempted in a subsequent iteration of the discovery process.

If another attempt is desired, then the master node delays until a first contention interval expires at delay operation 424. The first contention interval is an interval tracked by all master nodes to enable them to determine the start of a contention period when an exchange sequence has failed, such as this one where no RTS was received. Some nodes may have heard the RTS and therefore do not know whether the master expecting to receive the RTS received it or not so they must wait to start the contention until after the following DS message should be sent. So, once the first contention interval expires and the DS message has not been sent by that time, these other master nodes know the contention period has begun. The master node in the discovery process knows to start the contention period as well after delaying for the first contention interval at delay operation 424 since the master node already knows it will not be sending the DS message due to not receiving the RTS.

After delaying until the first contention interval expires, the master node then again contends for the carrier at contend operation 416. The logical operations then proceed for the same discovery access code as previously used. If query operation 422 determines that another attempt for this discovery access code should not be attempted, then query operation 426 determines whether there are additional discovery access codes to try. If so, then operational flow returns to contention operation 416 where after winning, the logical operations proceed with the next discovery access code. If query operation 426 determines that no additional discover access codes are available, operational flow proceeds to query operation 428.

At query operation 428, the master node detects whether to attempt another iteration of the discovery process. The number of iterations to attempt is another design choice. If many iterations are attempted, then all nodes are more likely to be discovered but more time may be wasted if all nodes are discovered in the first few iterations. If fewer iterations are attempted, then the chance of missing a node increases because on each previous iteration it may have sent an RTS that was not received due to a collision, such as because it and another node used the same discovery access code and transmitted an RTS at the same time. If query operation 428 detects that another discovery attempt is not necessary, then session access codes that have not been excluded during the previous iterations of the discovery process are assigned to node identifiers of slave nodes discovered during the discovery process so that communication with the slave nodes can be subsequently established at assign operation 444. The discovery process terminates, and the master node can proceed to initiate a communication session with one of the slave nodes that have been discovered. If query operation 428 detects that another discovery attempt is necessary, operational flow returns to generate operation 402 for the process to repeat.

Back at query operation 420, if the master node does receive an RTS, then the master node sends a CTS message with the discovery access code at CTS operation 430. If the CTS message is received, then the node being discovered knows to respond with the DS message. At query operation 432, the master node detects whether the DS message has been received from the node being discovered. If not, then the master node delays until the expiration of a second contention interval at delay operation 434.

The second contention interval is used by the master nodes to determine when an exchange sequence should end, i.e., when the ACK message should have been received, which is when the next contention period for all master nodes should begin. The master nodes know how long the second contention interval is based on the specified length of the DS message that is provided in the RTS and CTS messages as well as in the DS and ACK messages themselves, which the master nodes hear by eavesdropping. After delaying until the expiration of the second contention interval, the master node again contends for the carrier at contend operation 416, and proceeds again with the same discovery access code.

If query operation 432 detects that the DS message has been received, then when the DS message is from a master node, the master node of the discovery process obtains at data operation 436 the session access codes from the data field of the DS message and the node identifier of the master node that sent them. When query operation 432 detects that the DS message has been received and the DS message is from a slave node, then the master node obtains at data operation 436 the node identifier of the slave node that sent the DS message from the data field. The master node then sends an ACK message with the discovery access code at ACK operation 438.

If the master node has the session access code list of a master node, then the master node can exclude the session access codes of the list from the set of potential session access codes available for use at data operation 440 and save the node identifier of the master node for inclusion in DS messages of subsequent discovery iterations. If the master node has the node identifier of an available slave node, then the master node can queue the node identifier for subsequent association with a session access code at data operation 440 and save the node identifier of the slave node for inclusion in DS messages of subsequent discovery iterations. Operational flow then proceeds to query operation 442 where the master node again determines whether another discovery access code is available to try. If so, then operational flow returns to contend operation 416 where upon winning contention, the master node proceeds with the next discovery access code. If another discovery access code is not available, then operational flow returns to query operation 428 to determine whether another iteration of discovery is to be performed.

Figure 5:
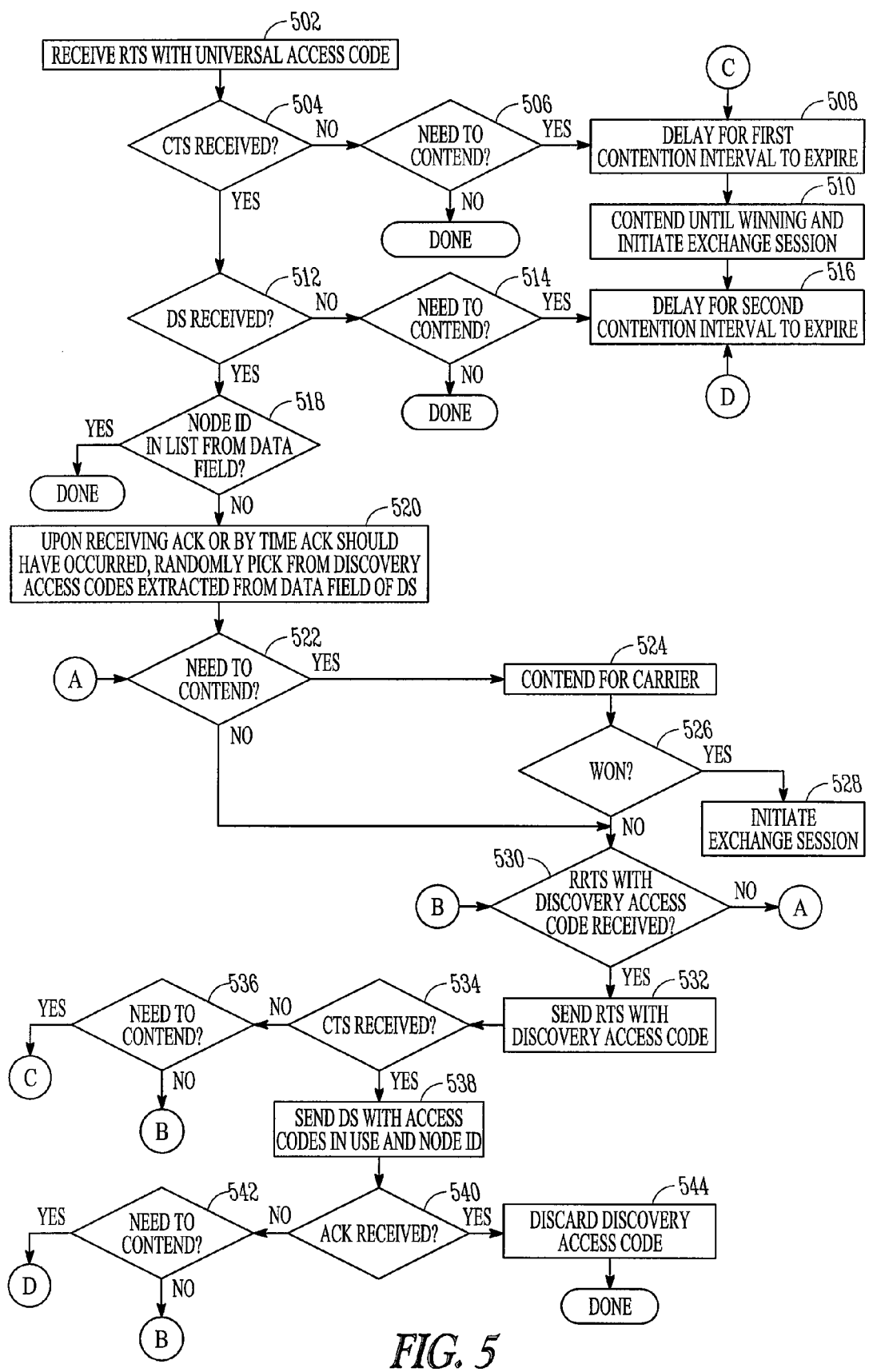
FIG. 5 shows illustrative logical operations performed by a master node being discovered by the master node implementing the illustrative logical operations of FIG. 4.

FIG. 5 illustrates the operational flow for a master node that is being discovered by a master node implementing the discovery process of FIG. 4. These logical operations begin at receive operation 502 where during a contention period, the master receives an RTS having a universal access code. This indicates to the master node that an exchange sequence such as discovery or a connect (discussed with reference to FIG. 7) is occurring within the network. The master node then detects whether a CTS message with the universal access code is received before a timeout expires at query operation 504. If not, then query operation 506 determines whether the master needs to contend for the carrier because it needs to send data or needs to request that a slave node send it data. If it does need to contend, then it delays for a first contention interval to expire at delay operation 508 and then contends until winning at contend operation 510. If contention is not necessary, then the master is done until it again determines to initiate a transmission or again receives an RTS at receive operation 502.

If query operation 504 detects that the CTS message has been received, then query operation detects whether a DS message with the universal access code has been received. If not, then query operation 514 detects whether the master needs to contend for the carrier. If not, then the master is done as discussed above. If the master does need to contend, then the master delays until expiration of the second contention interval at delay operation 516 and then contends until winning at contend operation 510.

If query operation 512 detects that the DS has been received, then query operation 518 detects whether the node identifier of the master node is found in the data field of the received DS message. If so, then the discovering master is already aware of this master and it need not reply to any further discovery messages from the discovering master, so this master is done as discussed above. If the node identifier is not in the data field, then this master has not been discovered yet. The data field of the DS message is indicative to the nodes in range of the discovering master node that the discovery process is occurring.

Upon receiving an ACK message with the universal access code or by the time the ACK should have been received, this master then randomly picks one of the discovery access codes from the data field of the received DS message at data operation 520. At query operation 522, the master node again detects whether it needs to contend. If so, it contends for the carrier at contend operation 524 and query operation 526 detects whether it won. Winning contention for the carrier is discussed in more detail below with reference to FIGS. 8 and 9. If this master has won contention, then it initiates an exchange session by sending a message at session operation 528 and proceeds. Sessions are also discussed in more detail below with reference to FIGS. 8 and 9. If this master has not won contention or if it does not need to contend, then operational flow proceeds to query operation 530.

If query operation 530 does not detect that an RRTS with the chosen discovery access code is received by the start of a next contention interval as detected by this master eavesdropping, then operational flow returns to query operation 522 to again determine if this master needs to contend for the carrier. If query operation 530 detects that the RRTS with the chosen discovery access code has been received, then this master node sends an RTS with the chosen discovery access code at RTS operation 532. Query operation 534 then detects whether a CTS message with the chosen discovery access code is received prior to expiration of a timeout. If not, then query operation 536 detects whether this master needs to contend. If so, operational flow returns to query operation 530, and if not, operational flow returns to delay operation 508.

If query operation 534 detects that the CTS message has been received, then the master node sends a DS message with the discovery access code and with the access codes in use by this master and the node identifier of this master at DS operation 538. At query operation 540, the master node detects whether an ACK with the discovery access code is received. If so, then the discovery access code is discarded by this master node at discard operation 544 since this master and its session access codes have been discovered. If not, then query operation 542 detects whether this master needs to contend for the carrier. If so, operational flow returns to query delay operation 516, and if not, operational flow returns to query operation 530.

Figure 6:
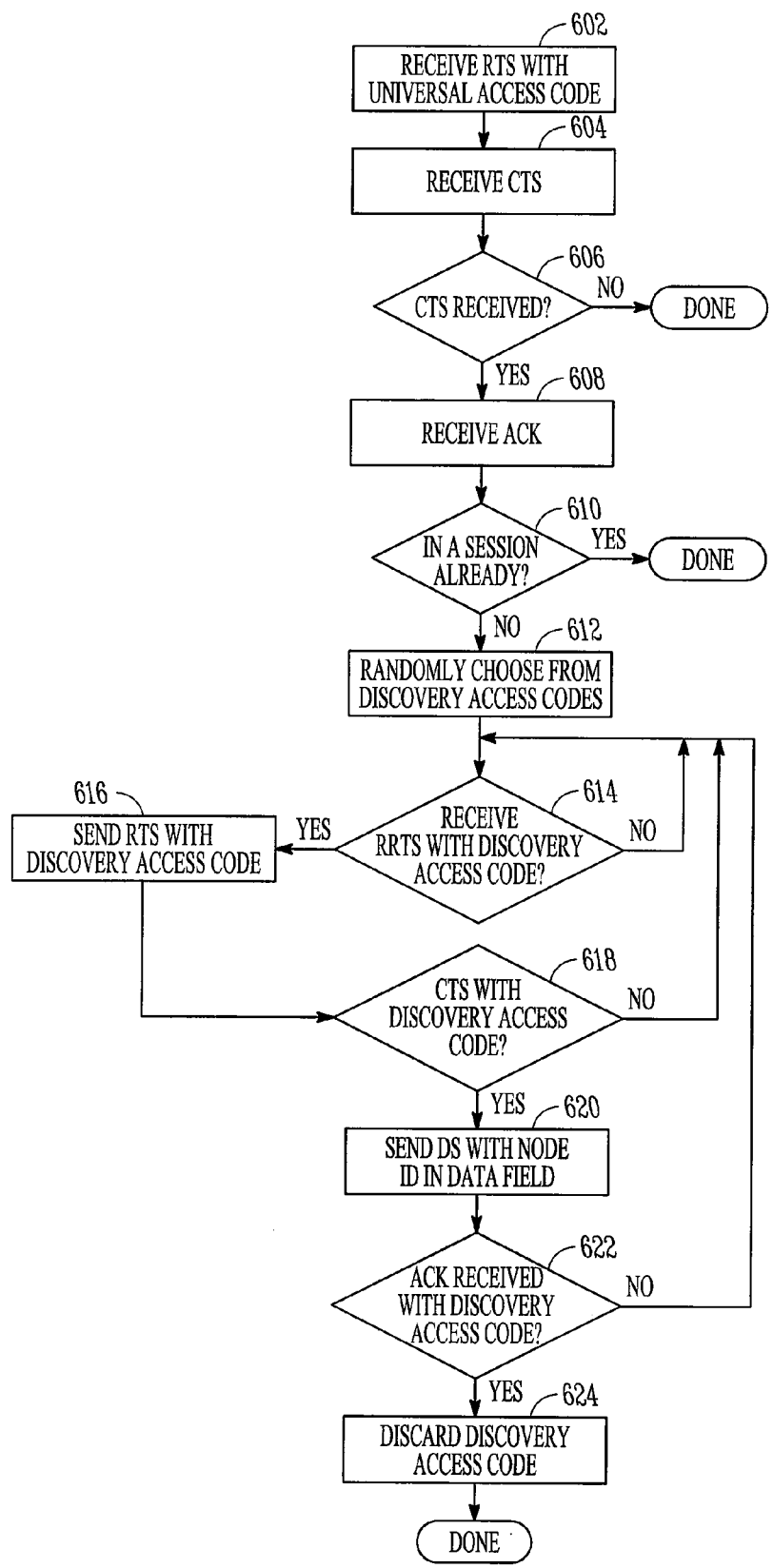
FIG. 6 shows illustrative logical operations performed by a slave node being discovered by the master node implementing the illustrative logical operations of FIG. 4.

FIG. 6 illustrates the logical operations performed by a slave node being discovered by the master node executing the discovery process of FIG. 4. These logical operations begin by the slave node receiving an RTS with a universal access code at receive operation 602. This RTS message indicates to the slave node that it is being discovered by a master node.

Upon receiving the RTS, the slave node waits until a CTS message with the universal access code is received at operation 604. Then query operation 606 detects whether the slave node has received a DS message with the universal access code. If not, then the slave is done until it hears another RTS or RRTS message. If so, then query operation 608 detects whether an ACK has been received. If so, then operation flow transitions to query operation 610.

Query operation 610 detects whether the slave node is already in a communication session with a master node. If so, then the slave node has an access code that has been assigned to it by a master node implementing a connection process discussed in more detail with reference to FIG. 7, and the slave is done as discussed above. If not, then the slave randomly chooses one of the discovery access codes extracted from the data field of the received DS message at data operation 612. Operational flow then proceeds to query operation 614.

At query operation 614, the slave node detects whether an RRTS message with the chosen discovery access code has been received. If not, the slave node continues to wait until the RRTS has been received or until another RTS with universal access code has been received since it is not in any session as this time. If so, then the slave node sends an RTS with the chosen discovery access code at send operation 616. At query operation 618, the slave node detects whether a CTS message with the discovery access code has been received within a timeout period. If not, the slave node continues to wait for the RRTS with the chosen discovery access code of RTS with the universal access code. If so, then operation flow transitions to DS operation 620.

At DS operation 620, the slave node sends a DS message with the node identifier of the slave node contained in the data field. Then at query operation 622, the slave node detects whether an ACK message with the chosen discovery access code has been received. If not, then the slave node continues to wait for the RRTS or RTS. If so, then the slave node discards the discovery access code at discard operation 624 since the slave node has been discovered by the master node.

Figure 7:
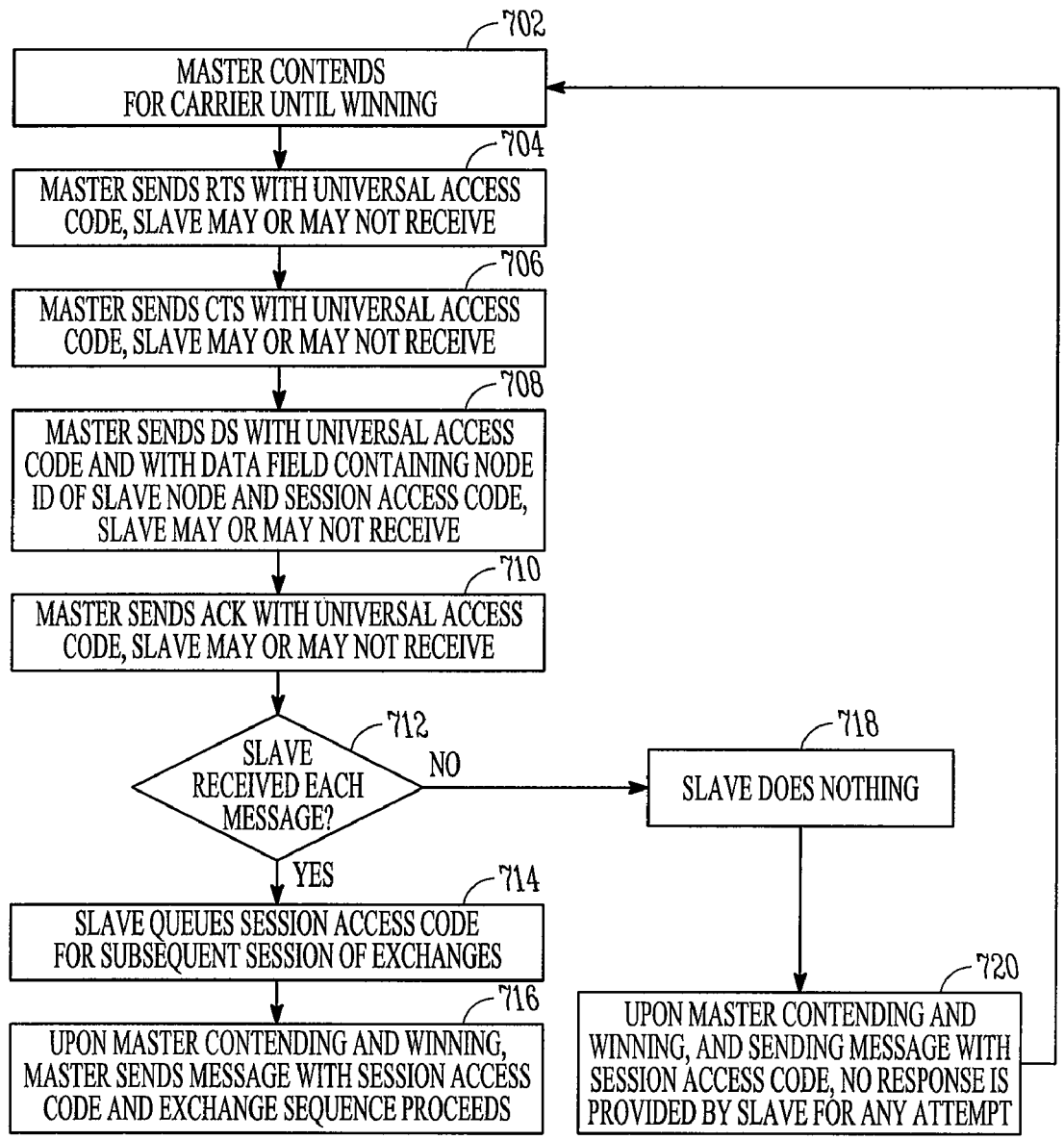
FIG. 7 shows illustrative logical operations performed by a master and slave node to establishing a communication session by setting a session access code.

FIG. 7 illustrates the logical operations of a master node establishing a connection with a slave node to begin a communications session. The established connection is the instruction to the slave node to become responsive to messages having a session access code that has been chosen by the master node for the slave node. The logical operations begin at contention operation 702 where the master node contends for the carrier until winning the opportunity to transmit on the carrier. Upon winning, the master node sends an RTS message with the universal access code at RTS operation 704. The slave node as well as all other nodes may or may not receive this message depending upon whether the message collided or if the slave or other node is out of range.

After sending the RTS, the master node sends a CTS message with a universal access code at CTS operation 706. Again, the slave node or other nodes may or may not receive this transmission. The master node then sends a DS message with the universal access code at DS operation 708. The data field of the DS message specifies that a session access code in the data field is to be utilized by a slave node with the node identifier also in the data field. The slave node and other nodes may or may not receive this DS message. For the master and slave nodes who do receive this message, the data field indicates that this is a connection process for a specific node identifier so all other nodes then ignore the connection process from this point onward except the master nodes continue to eavesdrop to determine the beginning of a contention period as discussed below for FIGS. 8 and 9. The master node performing operations of FIG. 7 then sends an ACK message with the universal access code at ACK operation 710. The slave node may or may not receive this message.

At query operation 712, the slave node identified by the node identifier has detected whether it has received each of the preceding messages sent by the master node. If not, then the slave node does nothing at state 718. Then, upon the master contending for the carrier and winning, the master sends a message (RTS or RRTS) with the session access code sent in the DS message at exchange operation 720 and receives no response since the slave has not become responsive to this session access code. The master may then reattempt the discovery process after reattempting to send an RTS or RRTS to the slave one or more times continues to fail.

If at query operation 712, the slave node identified by the node identifier in the DS message has detected that each of the preceding messages sent by the master node have been received, then the slave node queues the session access code for use during subsequent exchange sequences of a communication session with the master node at queue operation 714. Then, upon the master node contending for the carrier and winning and sending a message with the session access code, the slave will be responsive to the message if in range and if the message from the master node did not collide. An exchange sequence can then proceed at exchange operation 716.

Figure 8:
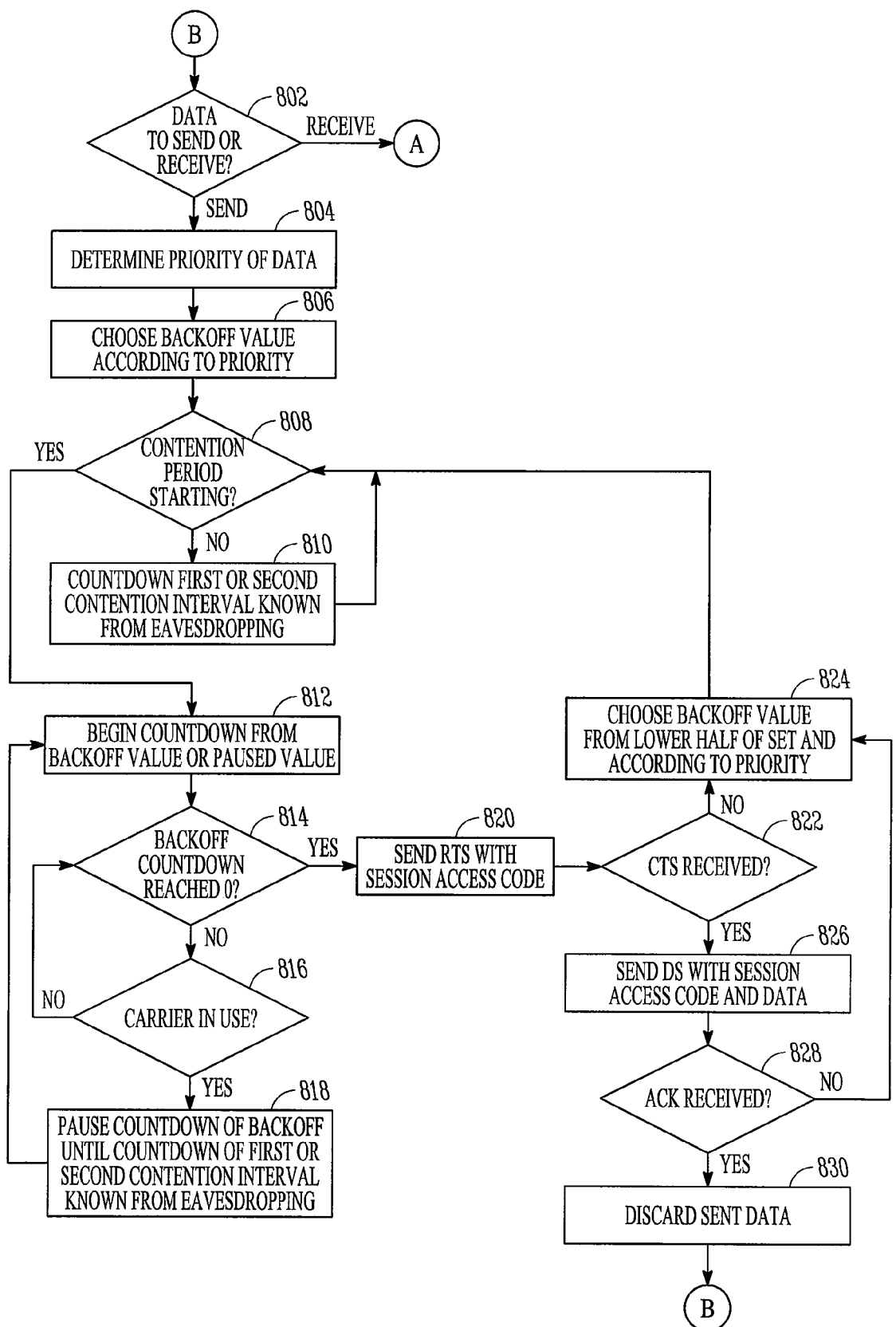
FIGS. 8 and 9 show illustrative logical operations performed by a master node to contend for the carrier of the network and then complete an exchange session with a slave node.
Figure 9:
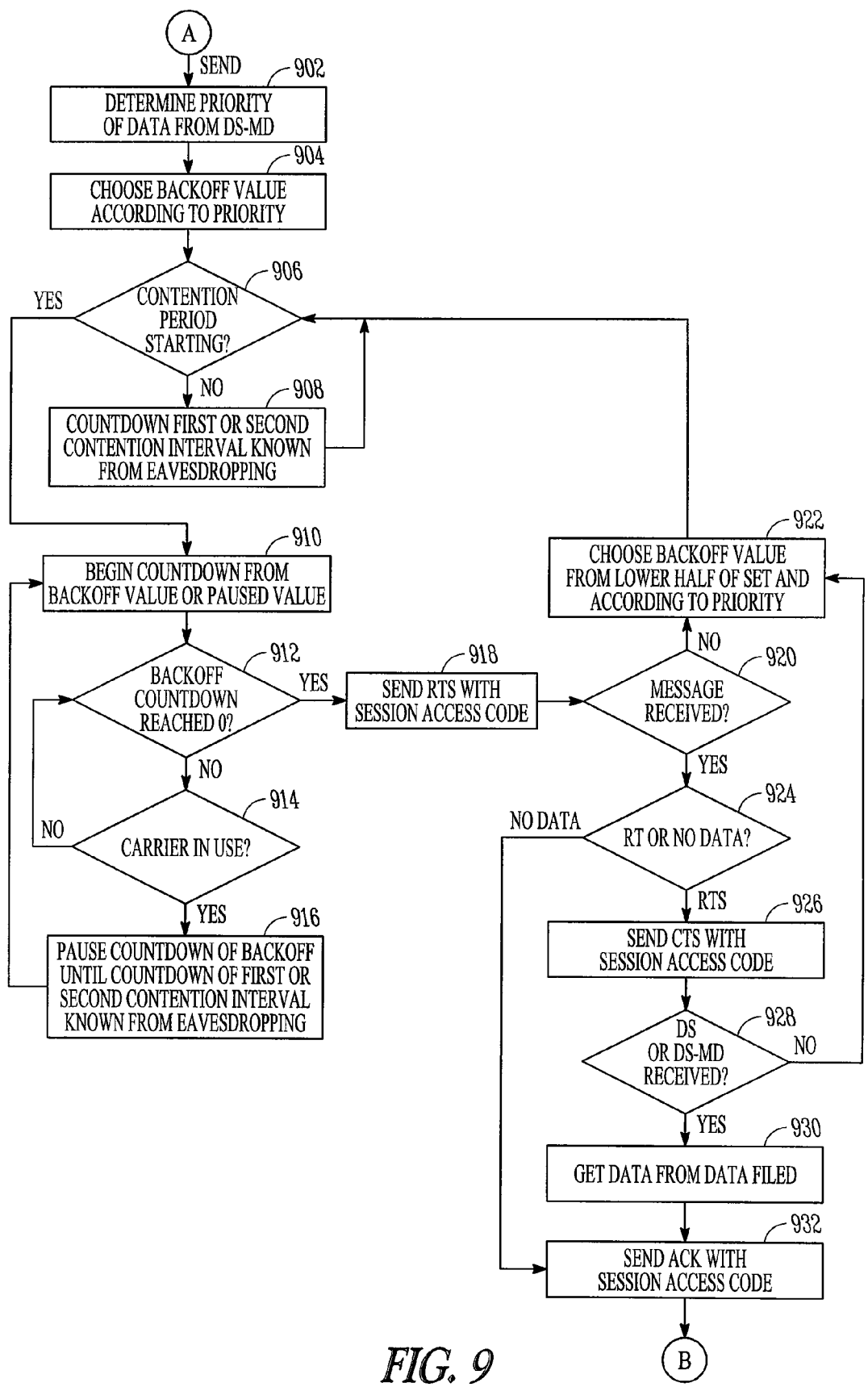

FIGS. 8 and 9 illustrate the logical operations that are performed by a master node when initiating an exchange sequence of a communication session with a slave node. The logical operations begin by the master node detecting whether to send data to the slave or receive data from the slave at query operation 802. This decision may be determined by the master knowing the priority of the data to send as indicated from a higher layer of the communication stack and may also be determined by whether the slave node has recently sent a DS-MD message that specified a given priority for the data that remains to be sent from the slave node or whether the polling interval has expired so that it is time to poll the slave for data.

If query operation 802 detects that data is to be sent to the slave node, then in embodiments where the decision at query operation 802 is not made with respect to the priority of data, then the priority of the data to send is determined at priority operation 804. If the priority is already known, then operational flow may proceed directly from query operation 802 to backoff operation 806. At backoff operation 806, the master node determines a backoff value by randomly choosing a value between a minimum and maximum. This range to randomly choose from may be pre-defined or may be dynamically determined depending upon various factors known by the master node, such as the number of master nodes also existing in the network. For more master nodes present, then the maximum may be set to a higher value. The minimum may be any value less than the maximum but is typically zero. Furthermore, the known priority of the data to send may be used to set the maximum such that the higher the priority of the data, the lower the maximum value for the range.

Upon randomly choosing a backoff value between the minimum and maximum, the master node then detects whether the contention period is starting at query operation 808. A master node existing with the network knows when a contention period is starting by knowing when its own ongoing exchange sequence, if any, is ending and by eavesdropping on at least transmissions of one node of an exchange sequence between two other nodes to learn when their exchange sequence, if any, will end. For ongoing communications of other nodes, the eavesdropping allows the master node to set the first contention interval and then, if necessary, set the second contention interval so that the master nodes of the network start their contention period that same time. Starting the contention periods at the same time gives affect to adjustments to choosing a backoff value based on priority of data to send or receive and/or based on the reattempt for an exchange sequence where a previous one failed. Also, using a first contention interval allows the contention period to start sooner where an exchange sequence has failed before completion, thereby saving time before the next exchange sequence begins.

As discussed above with reference to FIG. 4, the first contention interval is set by a master node so that the first contention interval expires once the DS or DS-MD message of an exchange should have started. This interval is set by the timing and type of message heard by eavesdropping. If an RTS is heard but not a CTS or if both the RTS and CTS are heard, the first contention interval is set by extending beyond the end of the RTS or CTS to account for the timeout periods and the transmission of the CTS to reach the point in time when the DS or DS-MD message should begin to be received. If the beginning of this DS or DS-MD message has not occurred by the expiration of the first contention interval, then the contention period begins for the master nodes of the network.

If the RTS is not heard but the CTS is heard through eavesdropping, then the master nodes must assume that the DS or DS-MD message will be sent so the first contention interval is not used to prevent transmitting and causing a collision with the DS or DS-MD message that may be coming from a hidden node. The second contention interval is then used to start the contention period for this master node not hearing the RTS. The second contention interval is also used when the RTS alone or RTS and CTS are heard and the DS or DS-MD message is also heard. The second contention interval is set to expire after the ACK message has been sent and is determined by accounting for the length of the DS or DS-MD message, the timeout period, and the ACK message.

If query operation 808 detects that the contention period is not starting, then the master node counts down the first contention interval and/or second contention interval as appropriate at countdown operation 810. If at the end of the first contention interval the DS or DS-MD message is received, then the query operation 808 detects that the contention period is starting. Likewise, if the second contention interval is reached and is expiring, then query operation 808 also detects that the contention period is starting.

Upon detecting that the contention period is starting, the master node begins counting down from the backoff value previously chosen or from a paused value that has occurred during the backoff countdown at countdown operation 812. The pausing of the countdown is discussed in detail below. While counting down from the backoff value or paused value, the master node continues to eavesdrop for messages sent by other nodes to start an exchange sequence. However, if the backdown count reaches a predefined win value as detected at query operation 814 before any of these messages are detected, then operational flow proceeds to RTS operation 820 as the master node has won contention for the opportunity to transmit on the carrier. The win value is typically zero but may be any value greater than or equal to the minimum of the backoff value range. If query operation 814 detects that the countdown has not reached the win value, then query operation 816 continues to eavesdrop for messages on the carrier while query operation 814 continues to detect whether the countdown has reached the win value.

Conversely, the master node may count up from the backoff value previously chosen towards the win value. In such a case, the win value would typically be the maximum of the backoff value range, but may be any value equal to or less than the maximum.

The count from the randomly chosen backoff value generally has the affect of spacing out the times when master nodes will attempt to transmit an initial message of an exchange sequence. For multiple master nodes, it is likely that each one will start a contention period with a different backoff value to count from so none will reach the win value at the same time. Thus, using the backoff counting reduces the collisions that occur within the network. However, if collisions do occur, another backoff value is chosen by each master node who transmitted simultaneously and it is likely that the backoff values chosen for the reattempts will be different so that a collision will not occur on the reattempt. The collision scenario where another backoff value is chosen is discussed in more detail below.

If query operation 816 of FIG. 8 detects that the carrier is in use prior to query operation 814 detecting that the countdown has reached the win value, then the master node pauses the backoff countdown at the current value (i.e., the paused value) and begins the first and/or second contention interval countdown at countdown operation 818 as described above for countdown operation 810. Upon the expiration of the appropriate contention interval thereby indicating the beginning of another contention period, the backoff countdown restarts from the paused value at countdown operation 812.

Once operational flow has transitioned to RTS operation 820 due to the backoff countdown reaching the win value, then the master node sends an RTS message with the session access code assigned to the slave that the master node wishes to send data to. Upon sending the RTS, the master node then detects whether a CTS with the session access code is received before expiration of a timeout at query operation 822. If not, such as due to a collision caused by another master reaching the win value at the same time, then the master node chooses another backoff value but from a range that extends to only a fraction (e.g., one-half) of the maximum at backoff operation 824. Thus, the backoff value has a high probability of being closer to the win value than the backoff value of the previous attempt such that the retry will most likely occur in a shorter period of time than it took for the previous attempt to occur. Furthermore, since the maximum is set based on the priority of the data, the fraction of the maximum is also affected by the priority such that the higher the priority of the data, the lower the backoff value for the reattempt will likely be. After choosing a new backoff value, operational flow returns to the query operation 808 to determine when to start the new contention period to begin the backoff countdown.

If query operation 822 detects that the CTS has been received, then the master node sends a DS message with the session access code and with the data to send to the slave included in the data field of the DS message at DS operation 826. Query operation 828 then detects whether an ACK with the session access code is received before expiration of a timeout. If not, then operational flow returns to backoff operation 824 where the master chooses the new backoff value for the reattempt. If the ACK is received, then the master may discard the data that has been sent at discard operation 830 since the slave has received the data. Operational flow then returns to query operation 802 to determine whether there is more data to send or whether there should be an attempt to request data from the slave node.

When query operation 802 detects that an attempt should be made to request data from the slave node such as because a DS-MD message was received in a previous exchange sequence or because the polling interval has expired, then operational flow proceeds to priority operation 902 of FIG. 9 where the master node determines the priority of the data to be requested from the slave if available from a previously received DS-MD message. Then, the master node chooses a backoff value between the maximum and minimum where the maximum is controlled by the priority of the data being requested at backoff operation 904. If the priority is relatively high, then the maximum is relatively low.

After choosing the backoff value, then query operation 906 detects whether the contention period is starting. If not, then at countdown operation 908 the first contention interval is set and/or the second contention interval is set as discussed above for countdown operation 810. Upon query operation 906 detecting the start of the contention period as described for query operation 808, then the countdown of the backoff value begins at countdown operation 910.

During the countdown, query operation 912 detects whether the countdown has reached the win value, such as zero, and query operation 914 continues to detect through eavesdropping whether the carrier is being used by other nodes to transmit a message. If query operation 914 detects use of the carrier prior to query operation 914 detecting that the countdown has reached the win value, then the master node pauses the countdown of the backoff until the expiration of the first or second contention interval indicates that the contention period is restarting at countdown operation 916.

Once the contention period restarts, the backoff countdown restarts from the paused value at countdown operation 910. Query operation 912 begins detecting whether the countdown reaches the win value while query operation 914 begins detecting whether the carrier is in use. Once query operation 912 detects that the countdown has reached the win value, then the master node sends an RRTS message with the session access code at RRTS operation 918 since the master node has won the opportunity to transmit on the carrier. Query operation 920 then detects whether a message with the session access code is received before expiration of a timeout.

When query operation 920 detects that no message has been received, such as because the slave node did not receive the RRTS due to a collision or being out of range or because the return message from the slave collided, then the master node chooses another backoff value but from a range that extends to only a fraction (e.g., one-half) of the maximum at backoff operation 922. As discussed above for backoff operation 824, this new backoff value has a high probability of being closer to the win value than the backoff value of the previous attempt such that the retry will most likely occur in a shorter period of time than it took for the previous attempt to occur. Furthermore, because the maximum is set based on the priority of the data, the fraction of the maximum is also affected by the priority such that the higher the priority of the data, the lower the backoff value for the reattempt will likely be. After choosing a new backoff value, operational flow returns to the query operation 906 to determine when to start the new contention period to begin the backoff countdown.

If query operation 920 detects that a message is received before expiration of the timeout, the query operation 924 detects whether the received message is an RTS or NO DATA message. If the message is an RTS message, this indicates to the master node that the slave does have data to send so the master node sends a CTS message with the session access code at CTS operation 926. Query operation 928 then detects whether a return message, namely a DS of DS-MD message is received prior to expiration of a timeout. If not, then operational flow returns to backoff operation 922 where a new backoff value is chosen. If the return message is received, then the master node gets the data from the data field at data operation 930 and then sends an ACK with the session access code at ACK operation 932. When query operation 924 detects that the message received after sending the RRTS is a NO DATA message, then operational flow proceeds directly to ACK operation 932. Once the ACK message has been sent, operational flow returns to query operation 802 of FIG. 8.

Figure 10:
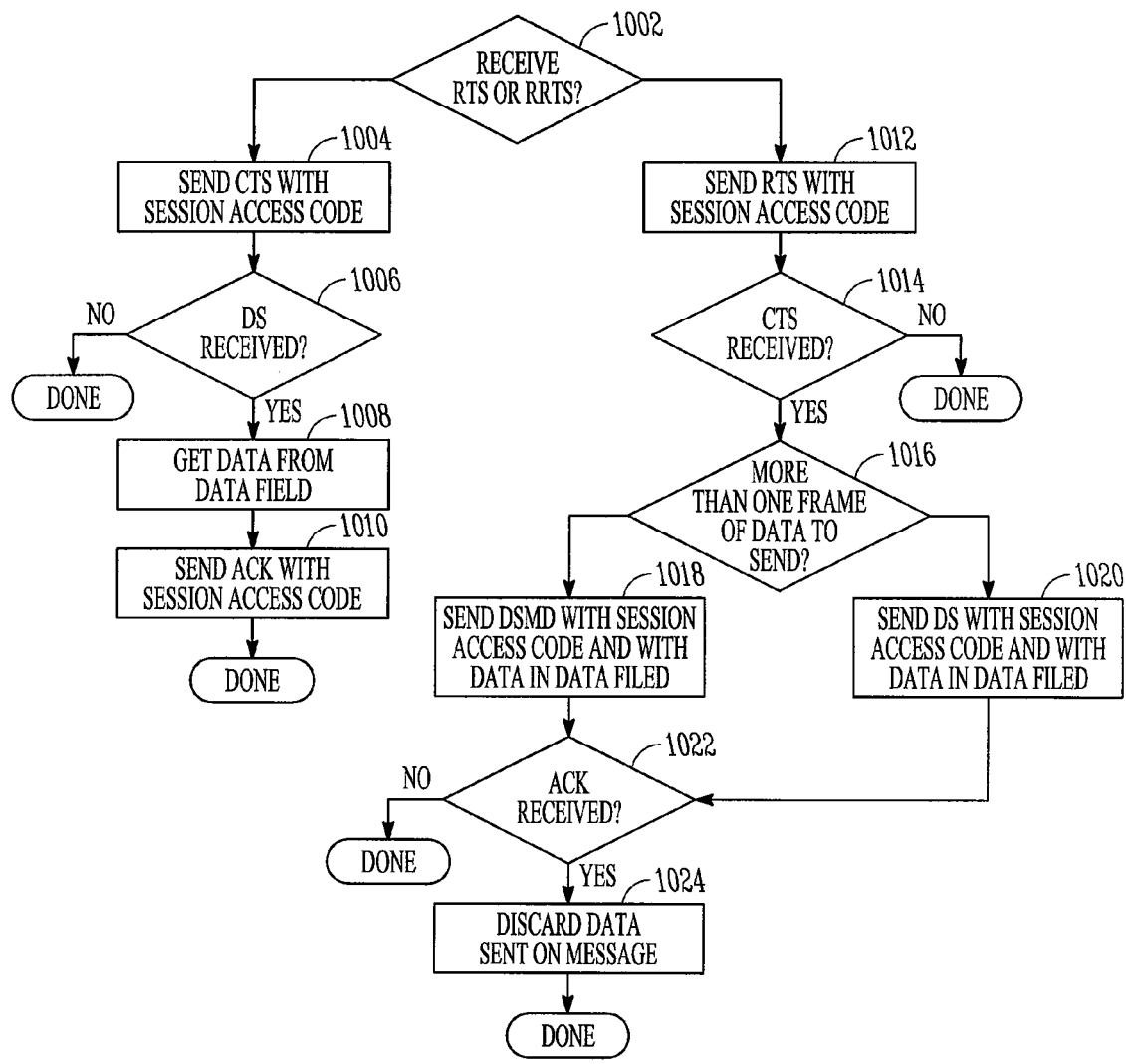
FIG. 10 shows illustrative logical operations performed by a slave node to complete the exchange session with the master node implementing the illustrative logical operations of FIGS. 8 and 9.

FIG. 10 illustrates the logical operations performed by a slave node in an exchange sequence of a communication session with a master node performing the logical operations of FIGS. 8 and 9. The logical operations begin by the slave node detecting whether it has received an RTS or RRTS message with its session access code at query operation 1002. If an RTS message is received, then the slave node sends a CTS message with the session access code at CTS operation 1004. Operational flow then proceeds to query operation 1006.

At query operation 1006, the slave node detects whether a DS message with its session access code is received before expiration of a timeout. If not, then the slave is done for this exchange sequence and then awaits another RTS or RRTS message to consider. If query operation 1006 detects that the DS message has been received, then the slave node gets the data from the data field of the DS message at data operation 1008. The slave node then sends an ACK message with its session access code at ACK operation 1010. The slave is then done for this exchange sequence.

When query operation 1002 detects that the received message with the proper session access code is an RRTS, then the slave node sends an RTS message with its session access code at RTS operation 1012. The slave node then detects whether a CTS message with its session access code is received prior to expiration of a timeout at query operation 1014. If not, then the slave is done for this exchange sequence. If the CTS message is received, then operational flow transitions to query operation 1016.

At query operation 1016, the slave node detects whether more than one frame of data is queued to be sent. If more than one frame of data is queued, then the slave node sends a DS-MD message with its session access code and with the first frame of data from the queue positioned in the data field at DS-MD operation 1018. Operational flow then proceeds to query operation 1022. If query operation 1016 detects that only one frame of data is queued for sending, then the slave node sends a DS message with its session access code and with the one frame of data positioned in the data field at DS operation 1020. Operational flow then proceeds to query operation 1022.

At query operation 1022, the slave node detects whether an ACK with the session access code of the slave node has been received prior to expiration of a timeout. If not, then this indicates that the master node may not have received the DS or DS-MD message and therefore the slave may need to send the data again. The slave node finishes the exchange sequence at this point without having removed the sent data frame from the queue of data to send. Each frame of data exchanged between the master node and slave node has a sequence number that allows the receiving node to place the data frame in the proper sequence to pass the data up the communication stack properly. Thus, if the slave resends the same data frame on another attempt, the master node can place the data frame in its proper sequence or discard it if in fact it had been properly received on a previous attempt.

When query operation 1022 detects that the ACK message has been received, then the slave node may discard the data frame in the queue that has been sent at discard operation 1024 since the master node has received this data frame. The slave node is then done for this exchange sequence and again waits to receive another RTS or RRTS message to consider.

Figure 11:
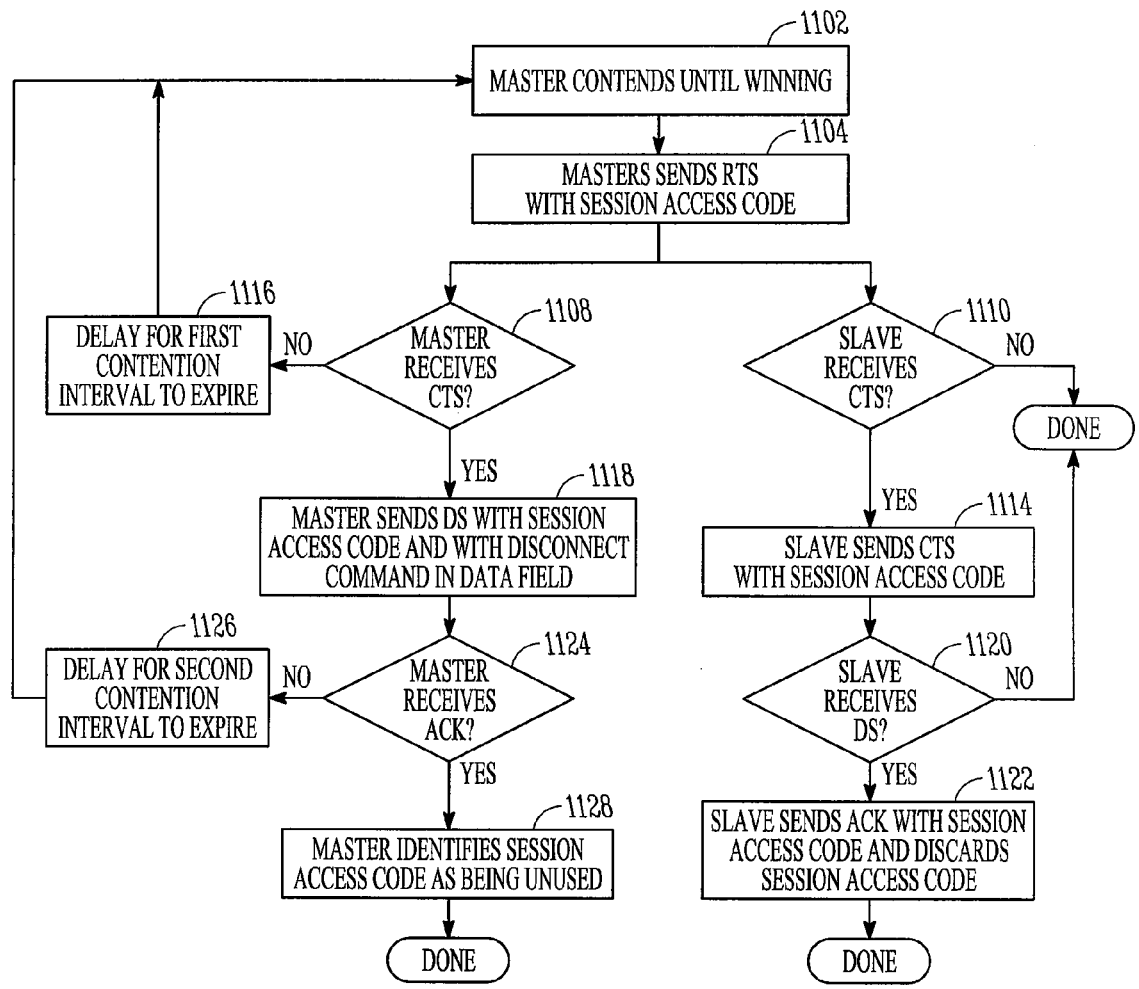
FIG. 11 shows illustrative logical operations performed by a master and slave node to terminate the communication session by stopping use of the session access code.

FIG. 11 illustrates the logical operations performed by a master and slave node in a communication session to disconnect the session so that no more exchange sequences will occur between these two nodes using the session access code currently in use between them. The logical operations begin at contention operation 1102 where the master node contends for the carrier until winning. Once the master node has won, it sends an RTS with the session access code at RTS operation 1104. The master node then begins to detect whether a CTS with the session access code is received prior to expiration of a timeout at query operation 1108.

Meanwhile, the slave node has been detecting whether an RTS or RRTS message has been received at query operation 1110. If no message has been received, such as due to no message being sent, being out of range, or the message colliding, then the slave node continues to be done until query operation 1110 finally does detect an RTS or RRTS message to consider. If query operation 1110 does detect an RTS or RRTS message with the session access code of the slave node, then the slave node sends a CTS message with the session access code at CTS operation 1114.

If the slave node at query operation 1110 continues to detect no message even though the master node has sent the RTS message at RTS operation 1104, no CTS message is sent by the slave node. The master then detects expiration of the timeout before receiving a CTS message at query operation 1108. The master node then delays for the expiration of the first contention interval at delay operation 1116 so as to find the start of the next contention period for master nodes of the network, and then operational flow returns to contention operation 1102 where the master begins to contend for the opportunity to transmit on the carrier again. As mentioned above, upon reattempts the master node will likely win sooner than on the previous attempt since the backoff value will likely be smaller.

If the slave node at query operation 1110 has detected the RTS message so that the CTS message is sent at CTS operation 1114, then the master node may detect the CTS at query operation 1108 unless the master node is out of range or the message has collided. If not received, then operational flow transitions to delay operation 1116 for the master node. If the CTS is received, then the master node sends a DS message with the session access code and includes a disconnect command in the data field at DS operation 1118.

After having sent the CTS message at CTS operation 1114, the slave node begins to detect whether the DS message has been received at query operation 1120. Query operation 1120 will not detect the DS message if the DS message collided which is unlikely, if the slave is out of range, or if the DS message was not sent because the master node never received the CTS message. If the DS message is not received, the slave is done for this exchange sequence. If the DS message is received, then the slave sends an ACK message with the session access code and then discards the session access code at ACK operation 1122 since it will no longer be used.

After having sent the DS message, the master node detects whether the ACK with the session access code is received before expiration of the timeout at query operation 1124. If so, then the master node identifies the session access code as being unused at code operation 1128 such that the session access code can be assigned to a slave node to communicate with through the connection process of FIG. 7.

However, the master node may not receive the ACK message if the ACK collided which is unlikely, if the master is out of range, or if the ACK was not sent because the slave node never received the DS message. If the ACK is not received, then the master delays until expiration of the second contention interval indicating the beginning of the next contention period and operational flow returns to contention operation 1102 for a reattempt at disconnecting. If the slave did receive the DS such that it discarded the session access code, then the slave node will never respond to the RTS message on each reattempt. Therefore, the master node repeats the reattempt process until a CTS response is repeatedly not detected at query operation 1108 after having performed delay operation 1126 at least once. The master node then identifies the session access code as being unused at code operation 1128 since it is presumed that the repeated lack of CTS responses is due to no slave having the session access code.

While the invention has been particularly shown and described with reference to illustrative embodiments thereof, it will be understood by those skilled in the art that various other changes in the form and details may be made therein without departing from the spirit and scope of the invention.

What is claimed is:

1. A method of discovering nodes to establish communication between a first master node and one or more nodes in a network medium used by a plurality of master nodes and slave nodes, wherein a slave node is an implantable medical device, wherein the plurality of master nodes contend for a carrier of the network medium, comprising:
   at a first master node, gaining use of the carrier;
   sending out a plurality of discovery access codes from the first master node;
   at the first master node, sending out a request for request to send message containing a first discovery access code of the plurality of discovery access codes, wherein the request for request to send message begins the communication sequence to obtain any available data from another node;
   at the first master node, listening for a request to send message containing the first discovery access code and sending out a clear to send message upon receiving the request to send message;
   upon receiving a data send message in response to the clear to send message at the first master node, when the data send message is from a second master node and includes a list of session access codes in use by the second master node, excluding the list of session access codes in use by the second master node from a list of potential session access codes at the first master node; and
   upon receiving the data send message in response to the clear to send message at the first master node, when the data send message is from a first slave node that includes identification information for the first slave node, storing the first slave node identification information in preparation for associating with a session access code that is not excluded from the list of potential session access codes at the first master node.

2. The method of claim 1, further comprising:
   at the first master node, gaining use of the carrier after sending out the plurality of discovery access codes but before sending out a request for request to send message containing the first discovery access code.

3. The method of claim 1, further comprising:
   after receiving the data send message, sending an acknowledge message from the first master node;
   after sending the acknowledge message, sending out a second request for request to send message containing a second discovery access code of the plurality, listening for a request to send message containing the second discovery access code, and sending out a clear to send message upon receiving the request to send message;
   upon receiving a data send message in response to the clear to send message at the first master node, when the data send message is from a third master node that includes a list of session access codes in use by the second master node, excluding the list of session access codes in use by the third master node from the list of potential session access codes at the first master node; and
   upon receiving the data send message in response to the clear to send message at the first master node, when the data send message is from a second slave node that includes identification information for the second slave node, storing the second slave node identification information in preparation for associating with a session access code that is not excluded from the list of potential session access codes at the first master node and that has not been associated with a node other than the second slave node.

4. The method of claim 1, wherein sending out a plurality of discovery access codes from the first master node comprises sending a request to send message with a universal access code followed by a clear to send message followed by a data send message containing the discovery access codes as data followed by an acknowledge message.

5. The method of claim 1, further comprising repeating the sending and receiving actions to send out a new set of discovery access codes and receive responses from master and slave nodes that did not previously respond successfully and receive no responses when all master and slave nodes did previously respond successfully.

6. The method of claim 1, further comprising:
prior to contending for the carrier at the first master node, monitoring for the carrier until a valid frame on the carrier is detected until at least two polling intervals have expired;
when a valid frame on the carrier is been detected before the at least two polling intervals have expired, delaying contending for the carrier until a message exchange between other nodes is detected to be complete; and
when at least two polling intervals have expired before a valid frame is detected on the carrier, beginning contending for the carrier.

7. The method of claim 1, including determining by a third master node when the communication sequence of the first master node will end according to the RRTS message.

8. The method of claim 1, wherein the data send message indicates that the sending node has more data to send.

9. The method of claim 1, wherein the data send message indicates that the sending node has additional data to send and indicates the priority of the additional data.

10. The method of claim 1, including
transmitting an acknowledge message from the first master node is response to the data send message; and
discarding the transmitted data at the transmitting node.

11. The method of claim 1, wherein gaining use of the carrier includes:
determining, by the first master node, whether the carrier is in use; and
contending for use of the carrier.

12. The method of claim 11, wherein determining whether the carrier is in use includes:
eavesdropping by the first master node on a current transmission of another node; and
determining by the first master node when the current transmission will end.

13. The method of claim 12, wherein contending for use of the carrier includes initiating a contention interval according to the determined transmission end.

14. The method of claim 13, wherein initiating a contention interval includes initiating a contention interval that will expire when a data send message is sent during a detected communication sequence.

15. The method of claim 13, wherein initiating a contention interval includes initiating a contention interval that will expire when an acknowledge message is sent during a detected communication sequence.

16. The method of claim 11, wherein contending for use of the carrier includes:
determining, by the first master node, a backoff value between a maximum back value and a minimum backoff value;
beginning, by the first master node, a count from the randomly chosen value towards a win value when the first master node detects that the carrier is not in use; and
transmitting the request for request to send message using the carrier when the count by the first master node reaches the win value.

17. The method of claim 14, wherein determining a backoff value includes determining a random value between the maximum back value and the minimum backoff value.

18. The method of claim 14, including:
determining, by the first master node, priority of data to be sent by the first master node; and
wherein determining a backoff value includes determining the backoff value according to the determined priority of data.

19. The method of claim 11, wherein contending for use of the carrier includes:
determining, by the first master node, a backoff value between a maximum back value and a minimum backoff value;
beginning, by the first master node, a count from the randomly chosen value towards a win value when the first master node detects that the carrier is not in use; and
pausing, by the first master node, counting towards the win value when it is determined that the carrier continues to be in use.

20. The method of claim 17, including:
continuing, by the first master node, the determining of whether the carrier is in use and the counting towards a win value according to the determined carrier use; and
transmitting the request for request to send message using the carrier when the count by the first master node reaches the win value.

* * * * *